United States Patent [19]

Wagner

[11] 4,389,578
[45] Jun. 21, 1983

[54] CONTROLLED GATE CIRCUIT

[76] Inventor: Delmer W. Wagner, 326 Pine Grove Rd., Rogue River, Oreg. 97537

[21] Appl. No.: 255,393

[22] Filed: Apr. 2, 1981

Related U.S. Application Data

[62] Division of Ser. No. 61,087, Jul. 26, 1979, abandoned, which is a division of Ser. No. 795,945, May 18, 1977, which is a division of Ser. No. 702,874, Jul. 6, 1976, Pat. No. 4,039,939.

[51] Int. Cl.³ ..................... H03K 17/74; H03K 5/00
[52] U.S. Cl. .................................. 307/256; 307/259; 307/359; 307/546; 328/127; 328/161
[58] Field of Search .............. 307/256, 259, 359, 546, 307/557, 562; 330/14, 5; 328/127, 128, 161

[56] References Cited

U.S. PATENT DOCUMENTS

| 3,249,766 | 5/1966 | Bourget | 307/256 |
| 3,591,851 | 7/1971 | Drushel | 307/359 |
| 3,694,668 | 9/1972 | Foerster | 307/359 |
| 3,710,142 | 1/1973 | Yokoyama | 307/256 |
| 3,857,048 | 12/1974 | de Meux et al. | 307/562 |
| 3,898,573 | 8/1975 | Sherman | 307/562 |

Primary Examiner—Stanley D. Miller
Assistant Examiner—B. P. Davies
Attorney, Agent, or Firm—Klarquist, Sparkman, Campbell, Leigh, Whinston & Dellett

[57] ABSTRACT

A moisture measuring apparatus includes a tuned circuit, a moisture sensor, coaxial cable means between the sensor and the tuned circuit wherein the tuned circuit tunes the coaxial cable, and a circuit for ascertaining the loading presented by the sensor to the tuned circuit whereby moisture is measured. The sensor is alternately connected and disconnected to an end of the coaxial cable and the signal drive across the tuned circuit is standardized by a controlled gate circuit which adjustably clips the tuned circuit drive, when the sensor is disconnected, for zeroing the instrument. Also, the gain of the circuitry is adjusted by periodically providing a standard load to the tuned circuit while adjusting amplification to bring about a standard output. The apparatus is not as sensitive to cable changes as prior apparatus and a plurality of selectable coaxial cables are provided on reels adjacent the sensor console.

8 Claims, 5 Drawing Figures

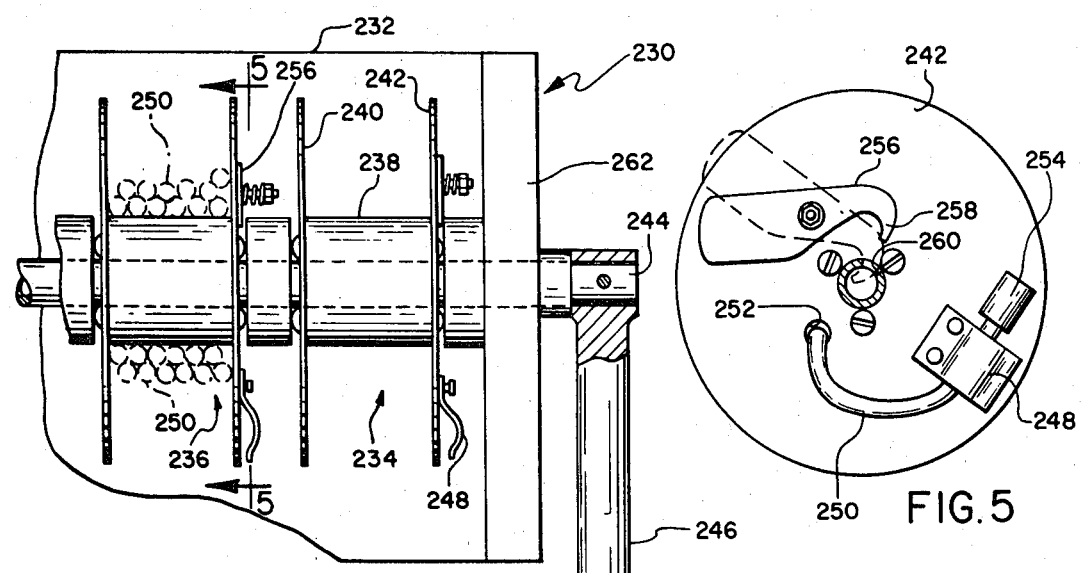
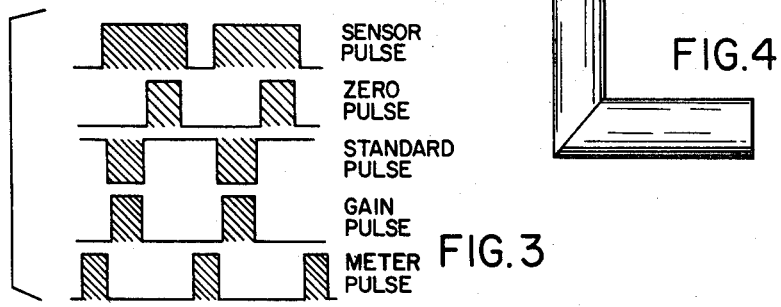
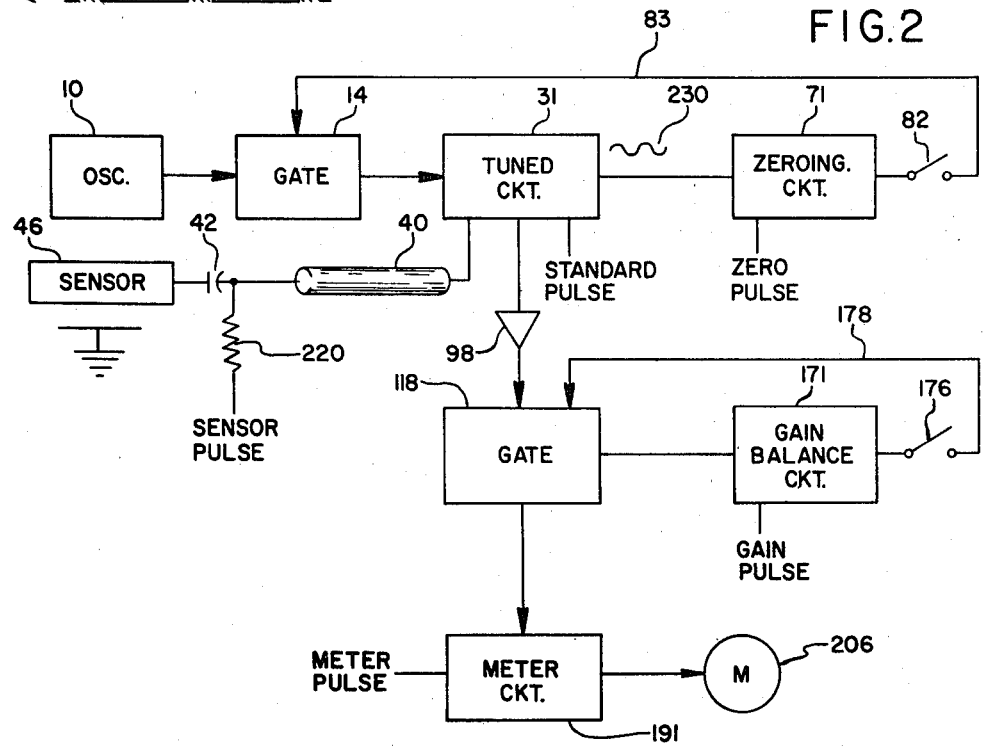

CONTROLLED GATE CIRCUIT

This is a division of application Ser. No. 061,087, now abandoned, filed July 26, 1979, which is a division of Ser. No. 795,945, filed May 18, 1977, which is a division of Ser. No. 702,874, filed July 6, 1976, now U.S. Pat. No. 4,039,939 issued Aug. 2, 1977.

BACKGROUND OF THE INVENTION

The present invention relates to a controlled gate circuit and particularly to a controlled gate circuit for adjusting the analog drive to a tuned circuit.

Moisture measuring apparatus has been known heretofore for taking moisture measurements by means of a sensor placed in a kiln wherein such sensor is connected to a meter circuit by an intermediate coaxial cable. The sensor would provide a shunting effect on a tuned circuit, according to the extent of moisture present, resulting in a measurement by a meter circuit. Unfortunately, circuits of this type are difficult to maintain in accurately calibrated condition since the presence of moisture is a relatively small parameter compared with other constants of the system. For example, the length of the coaxial cable between the sensor and the meter circuitry would have a pronounced effect on the calibration, and changes in length would require retuning of the circuit. Moreover, changes in circuit constants with age would have an effect on the calibration of the instrument requiring re-zeroing thereof. Generally, such equipment would be supplied with only one length of coaxial cable, although it might be more convenient to employ differing lengths of coaxial cable between the sensor and meter circuitry.

SUMMARY OF THE INVENTION

According to the present invention, a sensor is coupled to a tuned circuit on a periodic basis, while at other times the drive to the tuned circuit is standardized such that a given voltage is caused to appear across the tuned circuit. In a particular embodiment, a coaxial cable connects the sensor to the tuned circuit, but the sensor is disconnected from the far end of the coaxial cable while the drive is established. Then the only variable in tuned circuit loading becomes the sensor when the sensor is recoupled to the coaxial cable.

In particular, the drive to the aforementioned tuned circuit is supplied via a controlled gate circuit from an oscillator, and the gate is controlled from an integrating circuit that is set when the sensor is disconnected. The value set in the integrating circuit is such as to standardize the output across the tuned circuit when the sensor is disconnected therefrom for thereby standardizing the tuned circuit drive.

It is accordingly an object of the present invention to provide an improved moisture measuring apparatus which is less sensitive to circuit parameters, cable lengths and changes in cable humidity and temperature than apparatus heretofore available.

It is another object of the present invention to provide an improved moisture measuring apparatus which can be easily "centered" or "zeroed" for subsequent operation without requiring continued readjustment.

It is a further object of the present invention to provide an improved moisture measuring apparatus with which various lengths of coaxial cable can be employed.

It is a further object of the present invention to provide an improved gating circuit usable with moisture measuring apparatus or the like.

It is a further object of the present invention to provide an improved gating circuit for supplying standardized drive to a tuned circuit.

The subject matter which I regard as my invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

FIG. 2 is a block diagram of the FIG. 1 moisture measuring apparatus.

FIG. 3 is a waveform diagram illustrating a series of pulses applied to the circuitry of FIGS. 1 and 2, FIG. 4 is a reel array as may be employed with said moisture measuring apparatus, and FIG. 5 is a side view of one of the reels of the FIG. 4 array.

DETAILED DESCRIPTION

Figure 1:
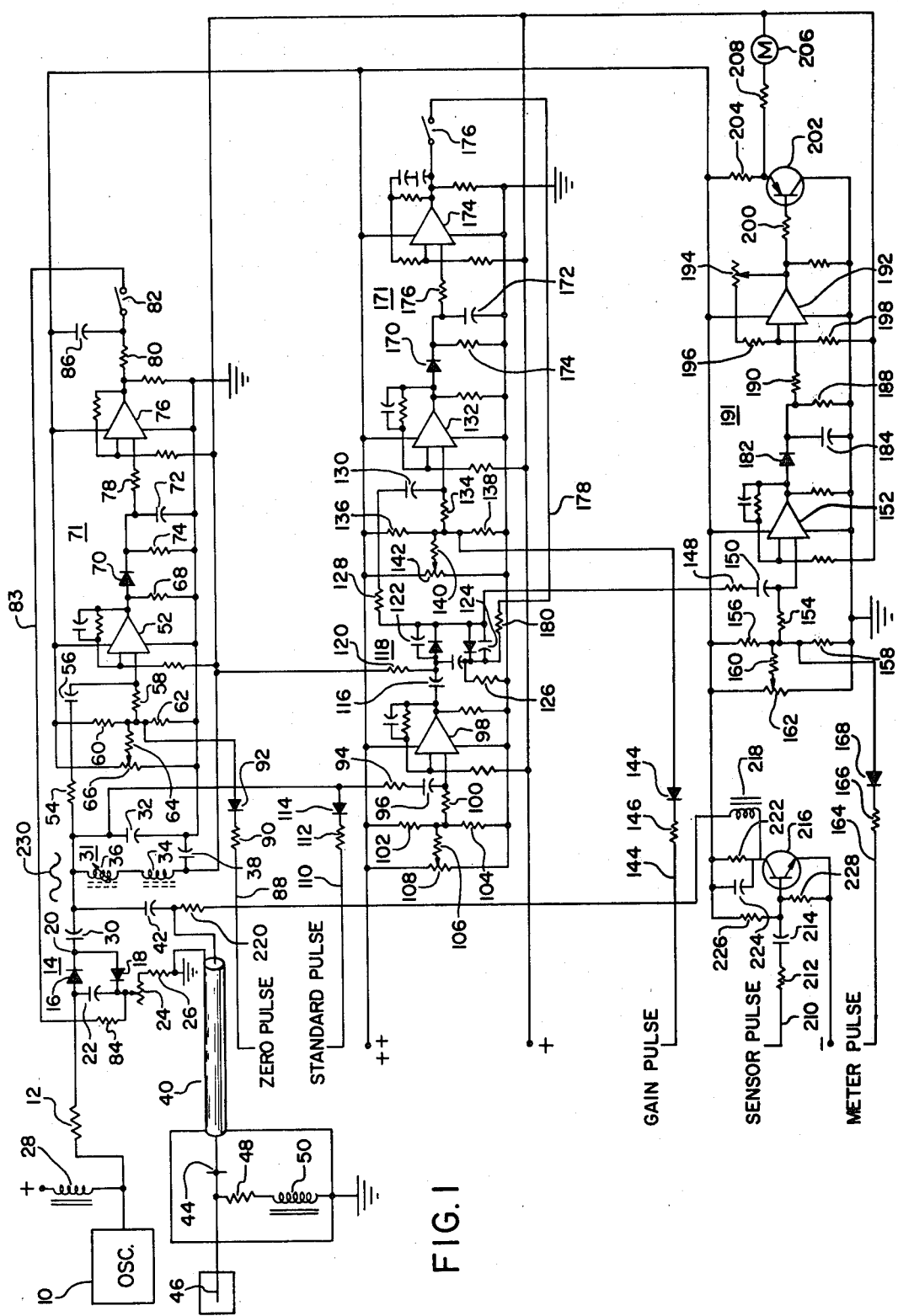
FIG. 1 is a schematic diagram of moisture measuring apparatus employing the present invention.

Referring to the drawings, particularly FIG. 1, RF oscillator 10 provides an input to the circuit and is connected via resistor 12 to diode gating circuit 14 including diodes 16 and 18 respectively having a cathode and anode joined to output terminal 20. Resistor 12 is connected to the anode of diode 16, and via capacitor 22 to the cathode diode 18. The cathode of diode 18 is also returned to ground via the series connection of potentiometer 24 and resistor 26. An RF choke 28 returns the output of oscillator 10 to a positive voltage.

The output terminal 20 of diode circuit 14 is coupled by means of capacitor 30 to one terminal of a parallel tuned circuit 31 comprising capacitor 32 shunted by the serial combination of inductance coil 34 and variable inductance coil 36, each suitably being provided with a ferrite core. A capacitor 38 is interposed between the remote end of coil 34 and the remote end of capacitor 32 which is also grounded. The tuned circuit is employed for tuning coaxial cable 40.

The outside terminal of coaxial cable 40 is grounded and the inner conductor is coupled to the junction between capacitor 30 and capacitor 32 by means of a coupling capacitor 42. At the remote end of coaxial cable 40, the center conductor is coupled via diode 44 to sensor 46 which is suitably disposed in a kiln or the like, while the juncture between the sensor and the diode is returned to ground via the series combination of the resistor 48 and choke 50.

The non-grounded end of the tuned circuit is also connected to an input of an amplifier 52 through resistor 54 and capacitor 56 in series, the input of the amplifier also being connected by resistor 58 to the center of voltage divider 60, 62, and further through resistor 64 to the movable tap of the potentiometer 66. A zero pulse lead 88 is connected through resistor 90 and diode 92 to the midpoint of the voltage divider 60, 62. Both the potentiometer and the voltage divider are disposed between a predetermined positive voltage and ground. A remaining input of amplifier 52, like other amplifiers in the circuit, is returned to the amplifier output and ground in a conventional fashion for integrated circuit amplifiers. A resistor 68 is disposed between the output of amplifier 52 and ground, while a diode 70 is interposed between the output of the amplifier and an integrating capacitor 72 shunted by resistor 74. The diode 70 is poled such as to charge capacitor 72 to a positive voltage at its ungrounded terminal. The ungrounded terminal of capacitor 72 is also coupled to an input of an amplifier 76 through resistor 78, the last mentioned amplifier having its output connected via resistor 80 to normally closed switch 82. The switch connects such output by way of resistor 84 in feedback fashion on lead 83 to the cathode of diode 18. A capacitor 86 is connected from the juncture of elements 80, 82 to a positive voltage. The circuit including amplifier 52 and 76 is designated as a zeroing circuit 71.

The ungrounded end of tuned circuit 31 is also coupled via resistor 94 and capacitor 96 in series to an input of an amplifier 98, said input also being coupled through a resistor 100 to the midpoint of a voltage divider 102, 104, and from such midpoint via a resistor 106 to a movable connection of potentiometer 108. A standard pulse lead 110 is further coupled to the ungrounded end of the tuned circuit through the series combination of resistor 112 and diode 114.

The output of amplifier 98 is coupled via capacitor 116 to a diode gate 118 connected in the same manner as diode gate 14, with the juncture of capacitor 116 and gate 118 being returned to a positive voltage through resistor 120. Also the diodes in gate 118 are shunted by capacitors 122 and 124 respectively, while a resistor 126 returns the gate to ground. A first output of gate 118 is coupled through resistor 128 and capacitor 130 in series to an input of amplifier 132 having its input connection further coupled by resistor 134 to the junction of a voltage divider 136, 138, and further through resistor 140 to the movable tap of potentiometer 142. Both the voltage divider and the potentiometer are disposed between a positive voltage and ground. A gain pulse lead 144 is connected through resistor 146 and diode 144 in series to the center tap of the voltage divider 136, 138. The output of gate 118 is further connected via resistor 148 and capacitor 150 to the input of an amplifier 152 which is also coupled by means of resistor 154 to the center tap of voltage divider 156, 158, and through resistor 160 to the movable tap of potentiometer 162, wherein the voltage divider and the potentiometer are disposed between a positive voltage and ground. A meter pulse lead 164 is coupled through resistor 166 and diode 168 in series to the center tap of the voltage divider 156, 158.

The output of amplifier 132 is connected through diode 170 to an integrating capacitor 172 shunted by a resistor 174. The ungrounded end of the capacitor is further coupled through resistor 176 to an input of amplifier 174 having its output coupled via switch 176 to a feedback lead 178 connected by way of resistor 180 to the junction of resistor 126 and gate 118. The circuit including amplifiers 132 and 174 is designated a gain balance circuit 171.

The output of amplifier 152 is connected through diode 182 to integrating capacitor 184 shunted with a resistor 188, the ungrounded end of capacitor being further coupled by a resistor 190 to an input of an amplifier 192. The amplifier 192 has a variable feedback circuit including potentiometer 194 and 196 disposed in series between the output of the amplifier and the remaining input terminal thereof, the latter being returned to ground through resistor 198. The output terminal of amplifier 192 is coupled via resistor 200 to the base of PNP output transistor 202 having its collector grounded, its emitter returned to a positive voltage hrough emitter resistor 204, and its emitter also being coupled to meter 206 through a resistor 208. The remaining meter terminal is returned to a positive voltage less positive than the voltage to which resistor 204 is connected.

A sensor pulse lead 210 is coupled through resistor 212 and capacitor 214 in series to the base of an NPN transistor 216 having its emitter connected to a negative lead and its collector coupled through RF choke 218 and resistor 220 in series to the juncture between capacitor 42 and the center lead of coaxial cable 40. The collector of transistor 216 is also returned to a positive voltage through the parallel combination of resistor 222 and capacitor 224, while a voltage divider comprising resistor 226 and resistor 228 is disposed between positive and negative voltages respectively, the center tap of which connects to the base of transistor 216.

The operation of the FIG. 1 circuit will be described with the aid of simplified block diagram FIG. 2 and waveform chart FIG. 3, the latter depicting repetitive waveforms which are provided on the various pulse leads by standard pulse generating circuitry (not shown).

As may be seen from block diagram of FIG. 2, oscillator 10 drives gate 14, the latter feeding tuned circuit 31 to an extent determined by means of feedback on lead 83 from zeroing circuit 71. The tuned circuit tunes coaxial cable 40 which drives sensor 46. The sensor conventionally comprises a plate or similar electrode placed among wood products in a drying kiln and utilized for measuring the moisture content of the wood products being dried.

In this case, the sensor 46 causes more or less loading upon tuned circuit 31, and this loading in turn causes a greater or lesser signal to be transmitted to gate 118 and from there through meter circuit 191 to meter 206. The zeroing circuit 71 is employed for maintaining predetermined drive conditions for the tuned circuit, in spite of moderate changes in coaxial cable 40 as may be interposed between the sensor and the tuned circuit, and regardless of variations in the magnitude of the output from oscillator 10. Moreover, the zeroing circuit 71 is employed for balancing the system to provide a predetermined reading or output on meter 206 for predetermined moisture conditions.

The gain balance circuit 171 is also utilized in balancing the circuitry so that a standard gain output coupling is provided as in the case of a standard loading of the tuned circuit. For this purpose, the standard pulse as depicted in FIG. 3 is applied to tuned circuit 31 for loading the same to a predetermined extent, at the same time the gain pulse is applied to gain balance circuit 171, with switch 176 being closed. Under these conditions, the gain of the circuit is set for a desired output. With switch 176 closed the signal magnitude for the standard pulse is maintained through gate 118 by means of feedback on lead 178. Since circuit 171 includes integrating capacitor 172, the gain to the output meter can be maintained, as well, at times when the standard pulse and gain pulse do not occur.

As can be seen in FIG. 1, the standard pulse, which is negative going, causes diode 114 to conduct and places a predetermined load on tuned circuit 31. At this time, the gain pulse, which is positive going, enables amplifier 132 which is otherwise "pulled down" at its input through diode 144. The charge on capacitor 172 is determined through diode 170, charging the capacitor to a value which would cause a prescribed gain reading. Since switch 176 is closed, the voltage on the lead 178 causes gate 118 to conduct to a predetermined degree. If the output is otherwise than as desired, potentiometer 142 may be adjusted for establishing the proper charge on capacitor 172 and therefore the proper output. Since the proper charge on capacitor 172 will be maintained from one standard and gain pulse combination to the next, the gate 118 always attains the proper attenuation to supply the proper signal value despite changes in amplifier 98 and the like. During initial setup, a positive going meter pulse may be applied at the same time as the standard pulse-gain pulse combination for monitoring the desired calibration of the instrument. The gain balance circuit then holds the gain at the proper value.

During normal operation, a zero pulse occurs after each combination of the standard pulse and gain pulse. The zero pulse is a positive going pulse and allows conduction through amplifier 52, the input lead of amplifier 52 otherwise being "pulled down" to a negative value through diode 92. When amplifier 52 conducts, capacitor 72 is charged to a desired value through diode 70. This value is such as to achieve the proper peak-to-peak value of waveform 230 across tuned circuit 31. Correct drive is maintained by means of feedback on lead 83, as hereinbefore indicated, such that gate 14 couples greater or lesser energy from oscillator 10 to the tuned circuit for maintaining the desired operation regardless of changes in the circuit, changes in the coaxial cable 40 coupled thereto, or changes in the magnitude of the waveform actually produced by oscillator 10. Since the proper drive across the tuned circuit for acquiring proper readings will be maintained largely independently of the coaxial cable 40 employed, a moderate change can be made in the length of cable 40 without readjusting the circuit. The feedback also keeps the meter in the "center of balance". It is understood the charge on capacitor 72 remains between applications of the zero pulse.

When the zero pulse is applied it is understood the sensor 46 is not connected to the circuit, i.e., the positive going portion of the sensor pulse disconnects diode 44 at this time via transistor 216, choke 218 and resistor 220. The other side of diode 44 is referenced to ground via resistor 48 and choke 50. Then, when the proper reference voltage has been established across tuned circuit 230, and the proper gain is established for the circuit including amplifier 98 between the tuned circuit and the meter circuit, the positive portion of the sensor pulse is discontinued, i.e., the sensor pulse goes negative. Consequently, diode 44 is allowed to conduct and the sensor 46 provides a load on the tuned circuit 31, and at this time changes the voltage across the tuned circuit. This voltage change is amplified via amplifier 98 and is passed on to the meter circuit 191 which operates meter 206. As a consequence, the meter 206 will constantly measure the moisture-caused loading of the tuned circuit and consequently the moisture in the kiln. The measuring circuitry itself is constantly standardized in performance and measurement ability by the preceding series of pulses.

As will be seen from FIG. 1, the output voltage of the tuned circuit, during measurement, is coupled via gate 118 to amplifier 152, the output of which is coupled to capacitor 184 by way of diode 182. Capacitor 184 stores the proper reading between occurrences of the meter pulse, which is applied to amplifier 152 substantially coincidentally with the negative going portion of the sensor pulse. The meter pulse causes diode 168 to stop conducting, whereby the input of amplifier 152, normally pulled down, is allowed to receive a signal. The positive going meter pulse is substantially concurrent with, but desirably somewhat narrower than, the negative going portion of the sensor pulse, so that the sensor is connected for the entire time the meter pulse is applied. The meter pulse causes amplifier 152 to conduct and capacitor 184 to store its charge. The charge on capacitor 184 is, of course, amplified by amplifier 192 which provides its output to transistor 202 for driving meter 206.

Gate 14, as well as gate 118, comprise a half-bridge diode gate which is turned on by negative voltage at its lower terminal. Considering gate 14 in particular, feedback on line 83 causes conduction of both diodes 16 and 18 from choke 28 through resistor 12 and through potentiometer 24 and resistor 26 to ground. So long as the voltage on line 83 is negative with respect to the voltage applied at the upper terminal of choke 28, the gate will conduct to some degree and the a.c. input is cooled either via diode 16, or via capacitor 22 and diode 18. However, the degree of conduction through the gate is dependent upon the value of the voltage on feedback leads 83. If the value of the voltage on lead 83 relative to the voltage supplied choke 28 is less than the peak to peak value of the oscillating waveform, then some clipping will take place, and the amount of clipping can be controlled by the value of the feedback voltage so as to control the energy supplied tuned circuit 31.

The actual sensor is energized via a coaxial cable as hereinbefore indicated. One or more such coaxial cables may be stored upon a cable reel configuration 230 as illustrated in FIGS. 4 and 5. This reel mechanism is suitably mounted on the underside of a console 232 in which the electronic circuitry, hereinbefore described, is located. The reel mechanism comprises a plurality of reels such as illustrated at 234 and 236, each including a central drum 238 to which end discs 240 and 242 are secured. The reels are rotatably received on an axial member 244, supported by a bracket 262 as may be mounted at one end of the console, and by another similar bracket (not shown) at the remote end of the console. A crank 246 is attached to one end of the axial member 244 for rotating the same, and each reel includes a catch 256 having a hook end 258 rotatable into locking engagement with an aperture 260 in rotatable member 240. The catch 256 is spring-loaded against the side of a reel disc so that it will remain in whatever position it is placed. Thus, the catch may be engaged for enabling rotation of the reels by means of crank 246, or the catch may be disengaged whereby the reel can turn freely.

On the side of each reel is mounted a clamp 248 for receiving one end of a coaxial cable 250 extending through aperture 252 in the side of the reel, and wherein the remote end of such coaxial cable receives a coaxial connector 254. This coaxial connector may be plugged into the electronic equipment (by means not shown), and the coaxial cable 250 in a given instance corresponds to the coaxial cable 40 as referenced in FIGS. 1 and 2. The coaxial cable is wound around one of the reels 234 or 236, and may be unwound for connecting the remote end thereof to a sensor in a given kiln. After connection to a sensor in a given kiln, the corresponding reel may be latched with catch 256 and coaxial connector 254 may be engaged with the electronic equipment for energizing the sensor and receiving information therefrom. When a cable is to be no longer used, the coaxial connector 254 may be disconnected, and the crank 246 turned to reel in the cable. Any one of a plurality of coaxial cables mounted on various reels may be coupled to the electronic equipment in a given instance without affecting the meter reading since the circuit is insensitive to all except large changes in the length of the coaxial cable. Thus, the zeroing circuit provides a given peak-to-peak voltage across the tuned circuit 31 at a time when the coaxial cable is connected, but at a time when the sensor is disconnected by means of diode 44. Then the only variable is the moisture which is sensed by the sensor. In this manner, variables attributable to most changes in cable length and changes in humidity and temperature of the cable are compensated for, and the tuned circuit doesn't have to be retuned for different cables. The meter is "balanced" or "zeroed" at a given reference reading and held there except for changes occasioned by moisture encountered by the sensor, which is the variable being measured.

While I have shown and described a preferred embodiment of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. A controllable gate circuit comprising:
   an input terminal and an output terminal,
   a first diode poled in the first direction between said input terminal and output terminal,
   a series connection of a capacitor and an oppositely poled diode disposed in that order between said input terminal and said output terminal,
   integrating circuit means for generating a gating signal having a relatively steady value,
   means for coupling said gating signal to the juncture between said capacitor and said oppositely poled diode to control the analog clipping levels of said diodes,
   and means for controllably varying said value of said gating signal from said integrating circuit means over a relatively continuous range to determine said clipping levels of said diodes and therefore to determine the degree of conduction between said input terminal and said output terminal.

2. The circuit according to claim 1 wherein said means for controllably varying periodically receives an output from said output terminal, said means for coupling comprising feedback means to adjust the analog conduction of the gate circuit to a predetermined level.

3. The circuit according to claim 2 including a tuned circuit driven from said output terminal and means for periodically loading said tuned circuit with an unknown load other than when said output is periodically received by said integrating circuit means for the purpose of detecting said unknown load while maintaining the drive of said tuned circuit.

4. The circuit according to claim 3 wherein said means for periodically loading said tuned circuit with an unknown load includes further gating means for periodically connecting and disconnecting said unknown load.

5. The circuit according to claim 2 further including an amplifier driving said input terminal, the output of which is to be periodically standardized.

6. A circuit for maintaining tuned circuit drive at a predetermined level, said circuit comprising:
   a controllable gate circuit having an input terminal, an output terminal and a gating control input,
   a tuned circuit driven from said output terminal,
   integrating circuit means for generating a gating signal having a relatively steady value,
   means for coupling said gating signal to said gating control input,
   and means for controllably varying said value to determine the degree of conduction between said input terminal and said output terminal, said means for controllably varying periodically also receiving an output from said output terminal.

7. The circuit according to claim 6 including means for periodically loading said tuned circuit with an unknown load for the purpose of detecting said unknown load.

8. The circuit according to claim 7 wherein said means for periodically loading said tuned circuit with an unknown load includes further gating means for periodically connecting and disconnecting said unknown load.

* * * * *